United States Patent [19]

Corley et al.

[11] 4,135,979

[45] Jan. 23, 1979

[54] TREATMENT OF XANTHAN GUM TO IMPROVE CLARITY

[75] Inventors: Foss E. Corley, La Mesa; Joe B. Richmon, El Cajon, both of Calif.

[73] Assignee: Merck & Co., Inc., Rahway, N.J.

[21] Appl. No.: 717,303

[22] Filed: Aug. 24, 1976

[51] Int. Cl.$^2$ .................. C12D 13/00; C12D 13/04
[52] U.S. Cl. .................. 195/31 P; 536/114
[58] Field of Search ............ 536/1, 114; 195/31 P

[56] References Cited

U.S. PATENT DOCUMENTS

| | | |
|---|---|---|
| 2,775,540 | 12/1956 | Wimmer et al. .................. 195/31 P |
| 3,355,447 | 11/1967 | O'Connell .................. 536/1 |
| 3,591,578 | 7/1971 | Colin et al. .................. 195/31 P |
| 3,773,752 | 11/1973 | Buchanan et al. .................. 195/31 P X |
| 3,964,972 | 6/1976 | Patton .................. 195/31 P |
| 4,010,071 | 3/1977 | Colegrove .................. 195/31 P X |

*Primary Examiner*—David M. Naff
*Attorney, Agent, or Firm*—Hesna J. Pfeiffer; Donald J. Perrella; Julian S. Levitt

[57] ABSTRACT

A xanthan gum fermentation beer containing at least about 1% gum is filtered at a temperature of at least about 112° C. The gum subsequently recovered from the filtrate has improved clarity.

11 Claims, No Drawings

TREATMENT OF XANTHAN GUM TO IMPROVE CLARITY

BACKGROUND OF THE INVENTION

1. Field of the Invention

The present invention relates to heteropolysaccharides produced by bacteria of the genus *Xanthomonas*. More particularly, the invention relates to a process for clarifying such heteropolysaccharides by filtration.

2. Description of the Prior Art

U.S. Pat. No. 3,355,447, issued to John J. O'Connell on Nov. 28, 1967, discloses a process for improving the clarity and stability of *Xanthomonas* hydrophilic colloids by heating a fermentation beer to a temperature from 66° C. to 77° C., holding the beer at this temperature for at least 20 minutes, cooling to a temperature in the range of 4° C. to 38° C., diluting to a concentration not above 1% and filtering. This process, however, is relatively time consuming and costly because of the requirement that the *Xanthomonas* hydrophilic colloid be diluted and filtered.

OBJECTS OF THE INVENTION

It is an object of the present invention to provide an improved method for clarifying a *Xanthomonas* hydrophilic colloid. Another object is to provide a faster and less expensive process for clarifying a *Xanthomonas* hydrophilic colloid. A further object is to provide a process which permits filtration of an aqueous solution containing above 1 weight % of *Xanthomonas* hydrophilic colloid. Still another object is to provide a process which does not require cooling the aqueous solution of *Xanthomonas* hydrophilic colloid before filtering.

SUMMARY OF THE INVENTION

In its broadest aspect the present invention comprises filtering at a temperature of at least about 112° C. a fermentation beer containing at least about 1 weight % xanthan gum, and also comprises the resulting beer.

DETAILED DESCRIPTION

The starting material for the process of the present invention is a *Xanthomonas* hydrophilic colloid solution and preferably a crude solution thereof known as a beer. A *Xanthomonas* hydrophilic colloid that is particularly suitable for use in accordance with the invention is such a colloid prepared by the bacterium *Xanthomonas campestris*. While *Xanthomonas campestris* is the bacterium of choice, nevertheless related species of *Xanthomonas* also elaborate a hydrophilic colloid which may be utilized. Such other species are, for example, *Xanthomonas begoniae, X. malvacearum, X. carotae, X. incanae, X. phaseoli, X. vesicatoria, X. papavericola, X. translucens, X. vasculorum*, and *X. hedrae*. These are all included within the scope of the present invention.

The *X. campestris* colloid is a polymer containing mannose, glucose, and potassium glucuronate. In such a colloid, the potassium portion can be replaced by several other cations without substantial changes in the property of the said material for the purpose. The colloid, which is a high molecular weight exocellular material, may be prepared by the bacterium *Xanthomonas campestris* by the whole culture fermentation of a medium containing 2-5 percent commercial glucose, an organic nitrogen source, dipotassium hydrogen phosphate and appropriate trace elements. The incubation time of the final medium is approximately 96 hours at 30° C. under aerobic conditions. In preparing the colloid as aforesaid, it is convenient to use corn steep liquor or distillers' dry solubles as an organic nitrogen source. It is expedient to grow the culture in two intermediate stages prior to the final inoculation in order to encourage vigorous growth of the bacteria. These stages may be carried out in media having a pH of about 7. In the first stage a transfer from an agar slant to a dilute glucose broth may be made and the bacteria cultured for 24 hours under vigorous agitation and aeration at a temperature of about 30° C. The culture so produced may then be used to inoculate a higher glucose (3%) content broth of larger volume in a second intermediate stage. In this stage the reaction may be permitted to continue for 24 hours under the same conditions as the first stage. The culture so acclimated for use with glucose by the aforementioned first and second stages is then added to the final glucose medium. In the aforesaid method of preparing *Xanthomonas campestris* hydrophilic colloid, a loopful of organism from the agar slant is adequate for the first stage comprising 290 milliliters of the glucose medium. In the second stage, the material resulting from the first stage may be used together with 9 times its volume of 3 percent glucose medium.

In the final stage the material produced in the second stage may be admixed with 19 times its volume of the final medium. A good final medium may contain 3% glucose, 0.5% distillers' solubles, 0.5% dipotassium phosphate, 0.1% magnesium sulphate having 7 molecules of water of crystallization, and water. The reaction in the final stage may be satisfactorily carried out for 96 hours at 30° C. with vigorous agitation and aeration. A *Xanthomonas* colloidal solution in the aforementioned stage of preparation is known as a beer. This is a preferred starting material for practicing the present invention, i.e., the beer resulting directly from the said fermentation may be used as starting material.

In accordance with the general method of the present invention an aqueous solution containing at least about 1 weight % of *Xanthomas* hydrophilic colloid (hereafter "xanthan gum") to be clarified, for example, a fermentation beer, is filtered at a temperature of at least about 112° C. up to a temperature beyond which thermal degradation of the gum occurs. Preferably the temperature is from about 112° C. to about 160° C., and most preferably from about 127° C. to about 149° C. It is preferred not to maintain the beer for prolonged times, e.g., beyond about 30 minutes, at elevated temperature in order to avoid degradation of the gum. The cooling may take place rapidly in a few minutes or slowly over a period of hours. For economical operation, however, it is preferred that the fermentation beer contain at least about 1.5 weight % xanthan gum. While the upper limit of xanthan gum is subject to variation, as a practical matter solutions containing above about 4.0% are too viscous to be filtered.

The filtrate obtained according to the present process is a clear solution substantially free of fermentation insolubles. The gum separated from this filtrate by conventional means, e.g., alcohol precipitation, spray drying or drum drying, is a highly clarified product suitable for all uses of xanthan gum and particularly foodstuff and pharmaceutical use as well as other uses where a clarified xanthan gum is required, e.g., in secondary and tertiary oil well recovery operations. The clarified fermentation broth itself which results from the hot filtration process of the present invention may also be used directly in such oil well recovery operations after appropriate dilution.

The following examples illustrate the present invention without, however, limiting the same thereto.

EXAMPLE 1

A sample (750 ml.) of fermentation beer containing 1.98 weight % xanthan gum is diluted with an equal volume of water. Filter aid (400 ml. of Johns Manville Hyflo Super-Cel) is added and the diluted beer is heated to 124° C. and filtered through a pressure leaf filter precoated with 400 ml. of a slurry of filter aid (Johns Manville Standar Super-Cel). The filtration takes about 5 minutes. The reconstituted gum has a light transmittance of 95% at 0.5 weight % as determined on a Klett Somerson colorimeter. Filtration at 82° C., by way of contrast, would be expected to take about an hour.

EXAMPLE 2

A sample in excess of 750 ml. of undiluted fermentation beer containing 2.09 weight % xanthan gum is heated to 121° C. in 15 minutes and filtered as in Example 1 but without dilution using an inlet pressure of 5.08 atmospheres. After 18 minutes, 750 ml. of filtrate are collected. The reconstituted gum has light transmittance of 89% at 0.5 weight % as determined on a Klett Somerson colorimeter.

EXAMPLE 3

To approximately 2,000 ml. of a fermentation liquor resulting from the fermentation process previously described and containing about 1.7 weight % of xanthan gum produced by the bacterium *Xanthomonas campestris* and having a viscosity of 3,150 cps at 24° C., there is added 25 g. of filter aid (Johns Manville Standard Super-Cel). The beer is heated to a temperature of 138° C. in 15 minutes in a pressure vessel and filtered through a 92.9 sq. cm. pressure leaf filter precoated with 15 g. of Johns Manville Hyflo Super-Cel using an inlet pressure of 5.08 atmospheres. After filtering for 12 minutes, 2000 ml. of filtrate are collected. The cooled filtrate is treated with isopropanol and the xanthan gum is recovered and dried in conventional manner. The reconstituted gum has a light transmittance of 66% at 0.5 weight % as determined on a Klett Somerson colorimeter. The light transmittance of a control sample is 50%.

EXAMPLE 4

Reconstituted xanthan gum is added to a fermentation beer having an initial xanthan gum concentration of 1.7 weight % to raise the concentration of xanthan gum to 2.7 weight %. A 2,000 ml. aliquot is then treated as described in Example 3. After filtering for 15 minutes, 1,800 ml. of filtrate are collected. The xanthan gum is recovered as described in Example 3. The reconstituted gum has a light transmittance of 68% at 0.5 weight % as determined on a Klett Somerson colorimeter. The light transmittance of a control sample is 39%.

EXAMPLE 5

To a 1,900 ml. sample of a fermentation liquor containing about 1.7 weight % of xanthan gum there is added 25 g. of filter aid (Johns Manville Hyflo Super-Cel). The beer is heated to a temperature of 138° C. in a pressure vessel and filtered through a 92.9 sq. cm. pressure leaf filter precoated with 15 g. of Johns Manville Hyflo Super-Cel using an inlet pressure of 5.08 atmospheres. After filtering for 3 minutes, 1,740 ml. of filtrate are collected. A 840 ml. aliquot of the filtrate is cooled rapidly to room temperature and treated with isopropanol to precipitate the xanthan gum which is dried and milled. The light transmittance of a 0.5 weight % solution of the reconstituted gum is 68% as determined on a Klett Somerson colorimeter. To the remaining 900 ml. of filtrate 10 g. of filter aid are added and the filtrate is reheated to 138° C. and again filtered as previously described. The cooled filtrate is treated with isopropanol to precipitate the xanthan gum which is dried and milled. The light transmittance of a 0.5 weight % solution of the reconstituted gum is 78% as determined on a Klett Somerson colorimeter while that of a 0.5 weight % solution of a control sample of xanthan gum recovered from the original beer is 14%.

What is claimed is:

1. A method for clarifying a xanthan gum produced by a bacterium of the genus *Xanthomonas* comprising filtering, at a temperature of at least about 112° C. up to a temperature beyond which thermal degradation of the gum occurs, a fermentation beer containing at least about 1.5 weight % xanthan gum, and separating the xanthan gum from the filtrate.

2. A method according to claim 1 wherein the beer contains from about 1.5 weight % to about 4.0 weight % xanthan gum.

3. A method according to claim 1 wherein the filtration takes place at a temperature of from about 112° C. to about 160° C.

4. A method according to claim 1 wherein the filtration takes place at a temperature of from about 127° C. to about 149° C.

5. A method according to claim 2 wherein the filtration takes place at a temperature of from about 112° C. to about 160° C.

6. A method according to claim 2 wherein the filtration takes place at a temperature of from about 127° C. to about 149° C.

7. A method according to claim 1 wherein the separation is effected by drying.

8. A method according to claim 7 wherein the drying is spray drying.

9. A method according to claim 7 wherein the drying is drum drying.

10. A method according to claim 1 wherein the separation is effected by alcohol precipitation.

11. A method according to claim 10 wherein the alcohol is isopropanol.

* * * * *